United States Patent [19]
Robson

[11] Patent Number: 5,251,622
[45] Date of Patent: Oct. 12, 1993

[54] RESPONSIVE PACEMAKER WITH TIME DOMAIN REFLECTOMETER AND METHOD OF USE

[75] Inventor: Jack R. Robson, Beech Grove, Ind.

[73] Assignee: Random Technologies, Inc., Indianapolis, Ind.

[21] Appl. No.: 971,281

[22] Filed: Nov. 4, 1992

Related U.S. Application Data

[63] Continuation-in-part of Ser. No. 866,850, Apr. 10, 1992, Pat. No. 5,231,987.

[51] Int. Cl.$^5$ .............................................. A61N 1/362
[52] U.S. Cl. ...................................................... 607/19
[58] Field of Search .................. 128/419 PG, 419 PT

[56] References Cited

U.S. PATENT DOCUMENTS

| | | | |
|---|---|---|---|
| 3,922,914 | 12/1975 | Fuchs ..................................... | 73/290 |
| 4,466,288 | 8/1984 | Grynberg et al. ..................... | 73/654 |
| 4,786,857 | 11/1988 | Mohr et al. .................. | 324/58.5 BO |
| 4,843,234 | 7/1989 | Berthold et al. ..................... | 250/227 |
| 4,893,895 | 1/1990 | Berthold et al. ..................... | 350/96 |
| 4,960,989 | 10/1990 | Liebenrood et al. ............... | 250/227 |
| 5,033,826 | 7/1991 | Kolner ................................. | 350/355 |

OTHER PUBLICATIONS

Tektronix 1502c Metallic Time Domain Reflectometer Service Manual Tektronix, Inc. Jul. 1991, pp. 5-1 to 5-11.
Quantum®II, Intermedics Cardiac Pulse Generator Physician's Model Models 253-25 and 254-30 Jan. 1990.
Pacesetter® Technical Manual-APSII Model 3000 Programmer with Model 3030 Function 1988.
Cordis Corp. 1986 "What de These Pagers Have In Common?".
Tektronix 1502c Metallic Time Domain Reflectometer Operator Manual May 1990.
Genesis® Cardiac Pacing System Model 285 Technical Manual Pacesetter Systems, Inc. 1985, #9190420-001.
Ventek® P AICD ™ Model 1600 Physician's Manual Automatic Implantable Cardioverter Defibrillator 1991 Cardiac Pacemaker Inc.
Hewlett-Packard Application Note 62, "TDR Fundamentals" Apr. 1988.
Hewlett-Packard Application Note 62-1, "Improving Time Domain Network Analysis Measurements", Apr. 1988.
Hewlett-Packard Application Note 62-3 "Advanced TDR Techniques" May 1990.

Primary Examiner—William E. Kamm
Attorney, Agent, or Firm—Baker & Daniels

[57] ABSTRACT

Responsive heart stimulating device and method for operating the device which includes a heart stimulating waveform generator for transmitting a waveform to an electrode. A time domain reflectometer (TDR) is also connectable to the electrode for generating TDR signals. A logic and control unit processes TDR readings from the electrode, and is adapted to alter the heart stimulating waveform in response to the TDR readings. The TDR may be connected to a pacemaker pacing electrode to detect changes in heart stroke volume or cardiac output, or to one or more probes capable of detecting motion of the patient, and the logic and control unit may adjust the pacing rate accordingly.

31 Claims, 7 Drawing Sheets

| NO. | READING DATE | COMMENTS | PHYSICIAN |
|---|---|---|---|
| 1/512 | 01/01/92 | PRE-IMPLANT READINGS W/ TECHTRONICS 1000 | SMITH, J. |
| 2/512 | 01/01/92 | IMPLANTED W/ TECHTRONICS 1000 ELECTRODE | SMITH, J. |
| 3/512 | 02/01/92 | POST-OPERATIVE CHECK-UP | SMITH, J. |
| 4/512 | 07/01/92 | 6 MONTH CHECK-UP OK | JONES, D. |
| 5/512 | 09/15/92 | PATIENT COMPLAINTS OF FATIGUE - CHECKS OK | SMITH, J. |

PRESS ▲ ▼ TO HIGHLIGHT, SELECT TO SELECT

FIG. 3

| ELECTRODE MANUFACTURER | MODEL NO. |
|---|---|
| CARDIAC PACEMAKERS, INC. | CPI 1000 |
| CARDIAC PACEMAKERS, INC. | CPI 1100 |
| INTERMEDICS, INC. | 254-001 |
| INTERMEDICS, INC. | ELECPRO 100 |
| PACESETTER SYSTEMS, INC. | PACE-3000 |

PRESS ▲ ▼ TO HIGHLIGHT, SELECT TO SELECT

FIG. 4

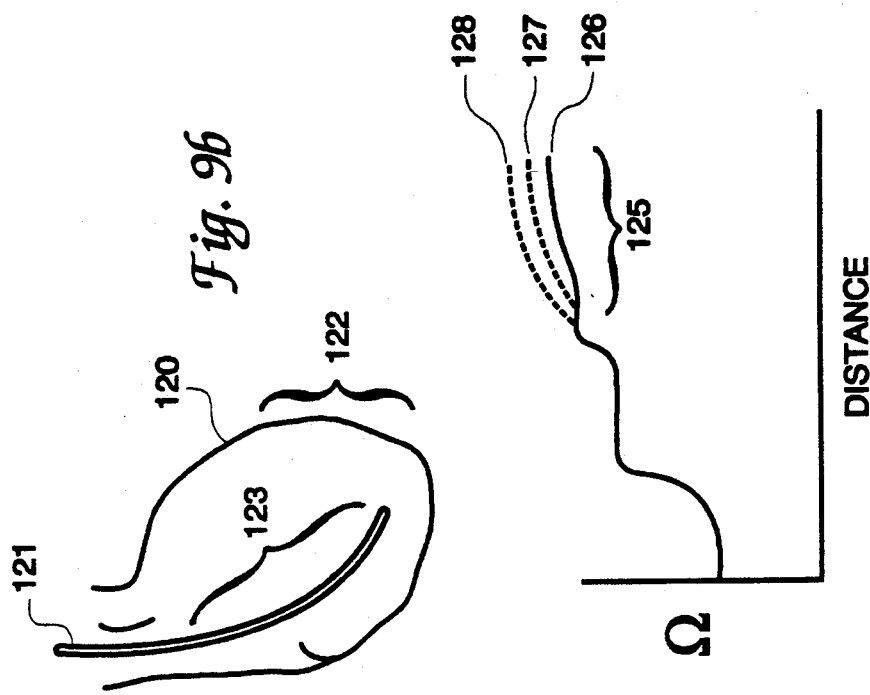
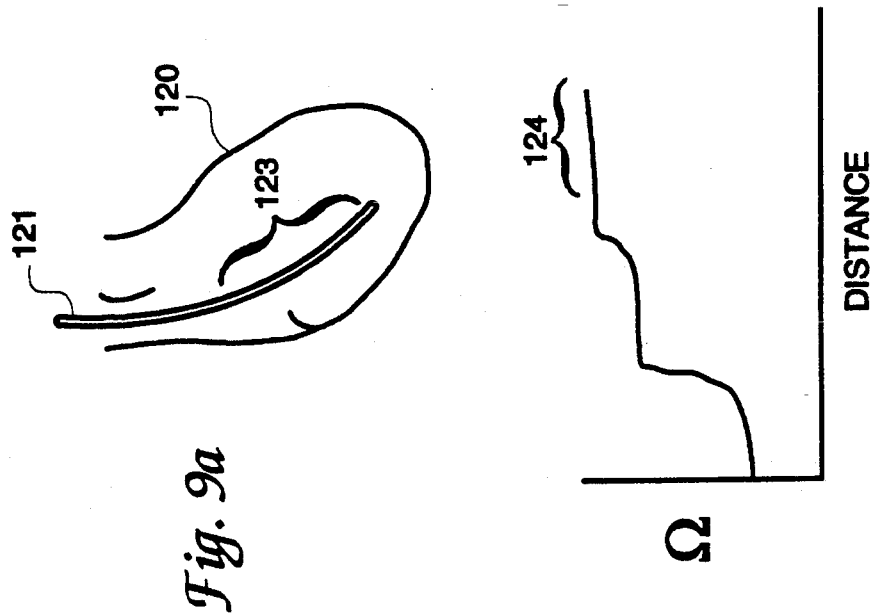

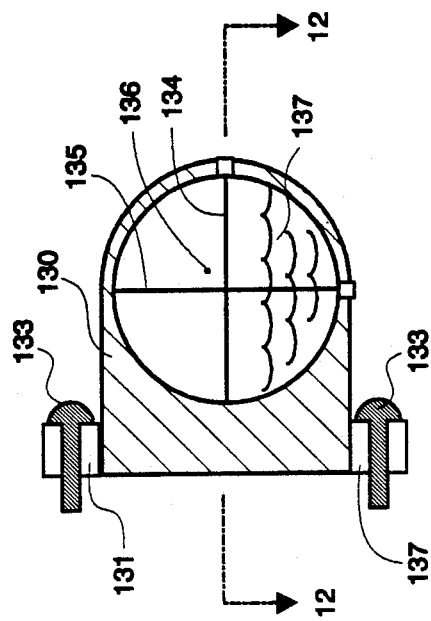
Fig. 11
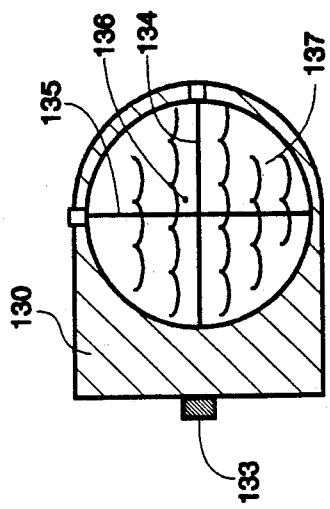
Fig. 12
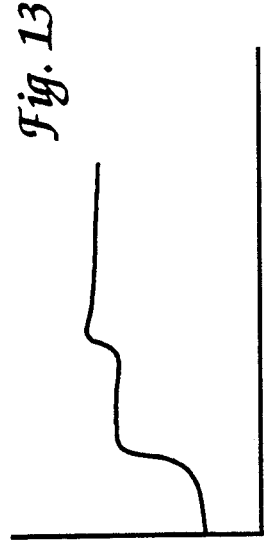
Fig. 13
Fig. 14
Fig. 15
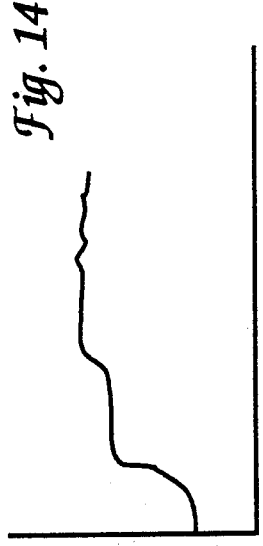

RESPONSIVE PACEMAKER WITH TIME DOMAIN REFLECTOMETER AND METHOD OF USE

CROSS REFERENCE TO RELATED APPLICATIONS

This is a continuation-in-part of application Ser. No. 07/866,850 filed Apr. 10, 1992, now U.S. Pat. No. 5,231,987.

FIELD OF THE INVENTION

This invention relates to a device, system and method used in medical equipment, and, in particular, to a responsive system for adjusting the waveform, such as the pacing rate, of a pacemaker in response to changes in physiological activity of the user.

BACKGROUND OF THE INVENTION

When a patient is provided with a pacemaker, the pacemaker may be designed to generate heart stimulating pulses continually, or only when the patient's natural heart rate falls below a predetermined rate or (internal) threshold. In either case, the generated pulses will occur at a predetermined rate (the "pace rate.") In addition, some pacemakers are "rate responsive," which means that they automatically adjust the pace rate if the patient's suspected physical activity increases or decreases. They are many different systems used in pacemakers to predict when a patient's physical activity has increased, and therefore, when the pacing rate should be increased.

Several systems for varying the pacing rate of a pacemaker work on the assumption that increased physical motion means that the patient is engaging in physical activity, and that the pacing rate must therefore be increased. For example, the Elite TM Models 7074, 7075, 7076, and 7077 manufactured by Medtronic, Inc. of Minneapolis, Minn., may be programmed to vary the pacing rate in response to detected changes in body motion. A sensor within the device, typically a piezoelectric crystal placed on the inside wall of the pacemaker, detects pressure waves within the body caused by body motion. The device then converts these pressure waves into electrical signals. The pacing rate is set in proportion to the frequency and amplitude of these electrical signals. Other systems, such as the Relay TM Models 293-03 and 294-03 manufactured by Intermedics, Inc. of Freeport, Tex., use an accelerometer instead of a piezoelectric crystal to detect physical motion. The accelerometer computes acceleration by measuring the force exerted by restraints that hold a mass in a fixed position. The accelerometer may either be electrically excited or self-generating, using a piezoelectric crystal as discussed above. Some systems also include multiple accelerometers oriented in different axes, so that movement in different directions can be discerned and used to reduce to obtain are more accurate indication of the extent of physical movement.

However, the theory behind motion sensitive rate-responsive systems is fundamentally flawed because physical motion does not necessarily mean that a patient's physical activity has increased. For example, motion-based responsive systems will increase the pacing rate when a patient is driving down a bumpy road, even though there is no increase in physical activity. Likewise, a patient may undertake significant physical activity that does not involve movement of the motion sensor, such as when performing bench presses with heavy barbells. In such circumstances, no physical motion will be detected so the pacemaker will not increase the pacing rate, even though an increase would be appropriate. In short, motion-based responsive pacemakers can not distinguish between motions that relate to increased physical activity and those that do not. Furthermore, if unnecessary pacing is activated by these devices, battery power consumption results in a shortened battery life. Shortened battery life may require a patient to undergo a surgical procedure to replace the battery sooner than may otherwise be required. It is also desirable to develop a rate-responsive system that requires little power to operate so as to extend pacemaker battery life.

Due to the shortcomings of motion-based rate responsive sensors, other rate adjusting systems are responsive to certain physiological conditions of a patient. Some pacemaker systems vary the pace rate based on changes in body temperature. These systems use a temperature sensing device such as a thermistor to sample the temperature of the body. The thermistor is built into an electrode of the pacemaker. The resistance of the thermistor varies as a function of temperature so that the device can generate an electrical signal that corresponds to the sensed temperature. This signal may be translated into a pre-programmed activity level used to set the pace rate.

However, body temperature sensitive systems also result in many of the problems that occur in motion sensitive rate-responsive systems as changes in body temperature may occur without regard to physical activity. Thus, the system may attempt to filter out such extraneous temperature changes. Yet, such a filtering system poses the risk that changes in temperature that should be used to vary the pacing rate will be ignored. Further, because the thermistor is built into a specialized electrode, that electrode can only be used with a pacemaker sold by a particular manufacture, thereby limiting the physician's and patient's choice of pacemakers. Due to cost and insurance regulations, it is not normally feasible to replace a previously implanted electrode or pacemaker. Thus, temperature responsive systems have the shortcomings of being poor predictors of a change in physiological activity, and of having only a limited choice of pacemakers from which to select.

Other systems, referred to as QT systems, adjust the pace rate by determining the activity level as measured by the QT interval measurement; that is, the time between when a pacing pulse is sent to the heart and the time the QT interval of the heartbeat begins. Generally, as a patient's physical activity increases, the heart responds more quickly to a pacing pulse. Therefore, QT systems increase the pacing rate when they sense that this time period is reduced. A particular shortcoming of QT systems is that in order to sense when pacing should be initiated or increased, they must actually send a pacing pulse to the heart, regardless of the patient's intrinsic heart rate. In general, it is medically undesirable to send pacing pulses to the heart unless it is known that the heart actually requires a pulse. In addition, unnecessary pulses also needlessly consume battery power.

Another type of rate-responsive system is based on measuring a patient's blood oxygen saturation levels. These systems assume that when a patient increases physical activity, there is a corresponding increase in the blood oxygen saturations level. These systems employ special electrodes equipped with a light emitting diode ("LED") and a phototransistor which measures the occlusion or blockage between the two. This blockage roughly corresponds to the amount of oxygen in the blood tissue. While the device is based on a physiological phenomenon, it has two drawbacks. First, the LED require a significant amount of power which reduces the life of the battery powering the pacemaker. Additionally, the system requires special electrodes that may lock the physician into the selection of a particular system.

Rate-responsive systems are also available which depend upon a patient's respiration to alter the pacing rate. These systems assume that increased air volume in the lungs means a patient is breathing deeper, suggesting that the patient is engaged in increased physical activity. Alt et al., "Function and Selection of Sensors for Optimum Rate-Modulated Pacing," *New Perspectives In Cardiac Pacing*, ed. Barold et al., 1991, p. 189–196. Specifically, such a system measures the respiratory rate by detecting the electrical impedance between an auxiliary electrode lead and the pacemaker can. Because the electrical conductivity of lung tissue decreases with inspiration, breathing can be detected by monitoring changes in electrical resistance. The resistance can be measured between different points within the system. One can apply a current between the pacemaker can and an anodal ring of a bipolar electrode so that the system measures the resistance change between the pacemaker can and the tip of the bipolar electrode.

However, one disadvantage of these respiration systems is their sensitivity to movement. For example, a respiration-dependent system is likely to detect high impedance changes if the pacemaker user moves his arms or has chest movements. Such measurements may be interpreted by the system as deep breaths that require an increased pace rate. Further, these system requires bipolar electrodes as one wire is needed to emit an RF wave and another wire is required to sense voltage.

Yet another type of rate-responsive pacemaker is based on the determination of changes in the stroke volume of the heart. Alt et al., p. 172–177. As an individual increases physical activity, the stroke volume of the heart increases, regardless of whether the heart rate remains constant due to a condition such as chronotropic incompetence. To measure stroke volume a specialized electrode having two or more electrode poles is positioned with the right ventricle. These impedance-based rate-responsive systems transmit a low-amplitude AC pulse or short intermittent electrical pulses to the multipolar electrode to measure resistance between the electrode poles. As resistance is affected by the amount of blood between the electrode poles, stroke volume is estimated. The pacing rate is increased when an increase in heart stroke volume is detected. However, these systems also have limitations. First, only a portion of the stroke volume may be measured as the measurements are dependent upon the position of the electrode pairs. Also, a multipolar rather than a unipolar electrode is required and the electrode must be carefully placed into position. Furthermore, stroke volume may only be measured for endocardial lead systems, i.e., those residing within the heart, but not for epicardial lead systems. Therefore, selection of a pacemaker that uses a specialized electrode is limited. Though stroke volume is a physiological phenomenon which accurately reflects the pacing requirements, it is desirable to provide a rate-responsive system using stroke volume which is not dependent upon the critical placement of multipolar specialized electrode. It is also desirable to provide a rate-responsive system which works in conjunction with both endocardial and epicardial lead systems.

OBJECTS OF THE INVENTION

Accordingly, it is one object of the present invention to provide a method to adjust the pacing rate of the pacemaker in response to physical activity level of the patient.

It is another object of the present invention to provide a system that measures the physical activity level of the user through a physiological phenomenon to avoid generating unnecessary pacing signals.

It is another object of the present invention to provide a pacing system that requires little power to operate.

It is still another object of the present invention to provide a pacing system that may use universal electrodes to insure user flexibility.

It is yet another object of the present invention to provide a pacing system which operates with both endocardial and epicardial lead systems.

It is yet another object of the invention to provide a pacing system that can also determine the physical and electrical integrity of the pacing electrode.

It is yet another object of the invention to provide a responsive pacing system that is responsive to heart stroke volume, cardiac output, physical motion, or any combination of the foregoing.

BRIEF DESCRIPTION OF THE DRAWINGS

FIG. 3 is a representative computer screen list window displaying an index of previous TDR readings which have been stored in the device.

FIG. 4 is a representative computer screen list window displaying a partial index of electrode manufacturers and models, one of which may be selected to provide a set of default electrode, sampling and display options for a particular electrode.

FIGS. 9a and 9b are views of a heart in which a pacemaker is implanted in which the heart is at its respective minimum and maximum stroke volumes.

FIGS. 10a and 10b are representative TDR readings from an electrode taken at times when the heart is at its respective minimum and maximum stroke volumes.

FIGS. 11 and 12 are side and top sectional views, respectively, of an enclosed chamber having liquid and TDR probes therein, and which acts as a motion sensor component.

FIGS. 13-15 are representative TDR readings from the TDR probes in FIGS. 11 and 12.

SUMMARY OF THE INVENTION

In one embodiment, the invention is a responsive heart stimulating device and method for operating the device which includes a heart stimulating waveform generator for transmitting a waveform to an electrode. A time domain reflectometer (TDR) is also connectable to the electrode for generating TDR signals. A logic and control unit processes TDR readings from the electrode, and is adapted to alter the heart stimulating waveform in response to the TDR readings. The TDR may be connected to a pacemaker pacing electrode to detect changes in heart stroke volume or cardiac output, or to one or more probes capable of detecting motion of the patient. One feature of the invention is that because cardiac chemistry affects the cardiac substrate which increases or decreased how hard the heart muscle contracts or relaxes, such changes can be detected and the a pulsing waveform may be modified accordingly.

DETAILED DESCRIPTION

Figure 1:
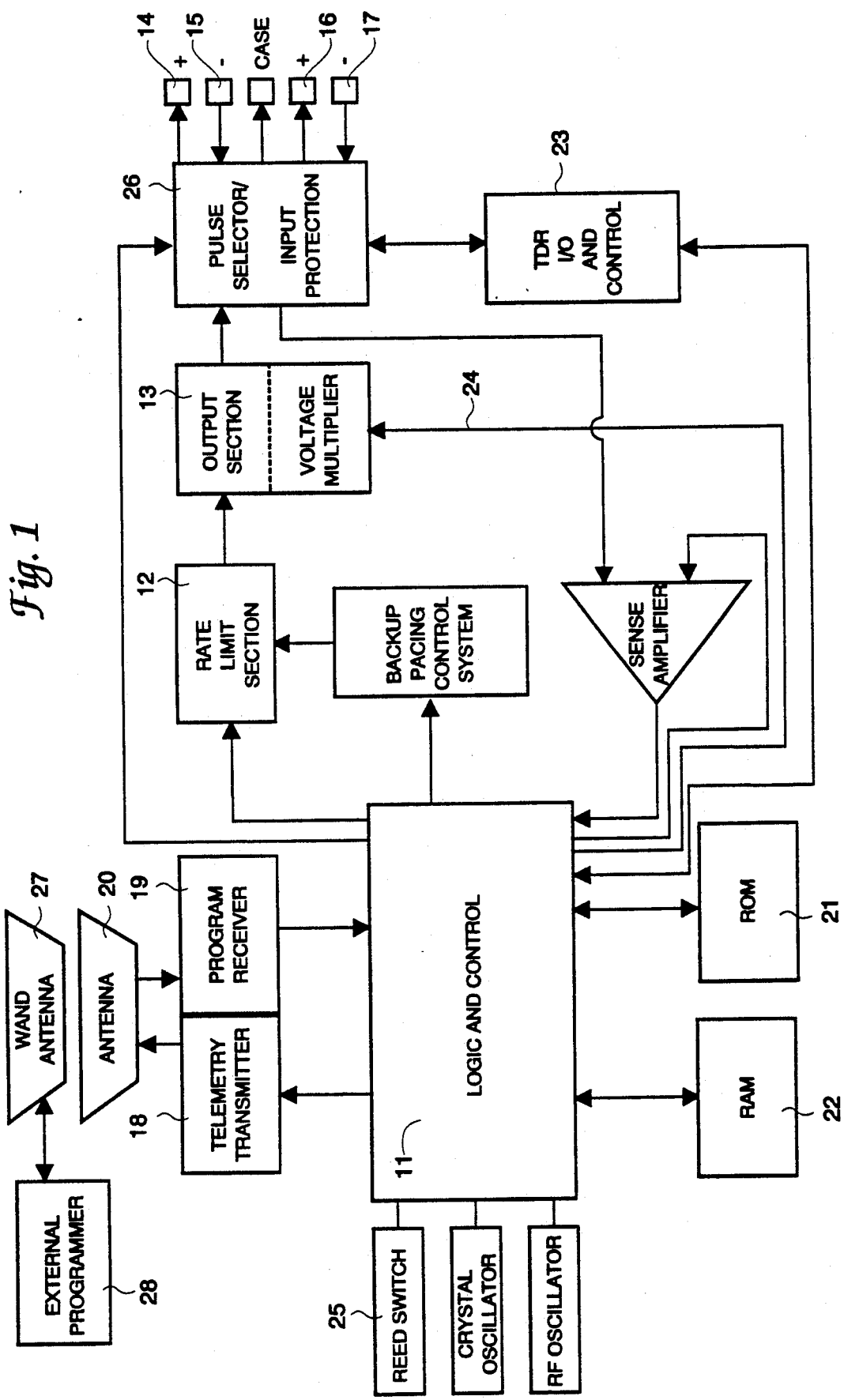
FIG. 1 shows a block diagram of one embodiment of a device of the present invention when used in connection with a programmable cardiac pacemaker.

Referring to FIG. 1, there is shown a representative block diagram of one embodiment of the present invention. In this embodiment, the invention is located in an implantable multi-programmable pacemaker, which includes logic and control unit 11 (which includes a CPU and appropriate software to carry out the functions described herein), rate limit section 12, and means for generating a heart stimulating waveform, namely output section/voltage multiplier 13. Conventional microcircuitry, and preferably, and application specific integrated circuit, is used to package the TDR and other components in the implantable case. The pacemaker is designed to provide periodic pulse to two implantable pacing electrodes through electrode receiving means, namely connectors 14 and 15, and 16 and 17 respectively. However, the invention may also be used with a device connected to a single electrode. Connected to logic and control unit 11 is a telemetry system comprised of telemetry transmitter 18 and program receiver 19, both of which on connected to common antenna 20. The telemetry system allows the pacemaker to be interrogated to determine its operating conditions after it has been implanted, and also allows the pacemaker to be reprogrammed without surgery. For example, the device can be reprogrammed to generate stimulating pulses on the pacing electrode at set rate, or at a varying rate depending on cardiac activity. Other parameters, such as the pulse width and pulse amplitude can also be specified after the pacemaker has been implanted. These operating parameters are stored in random access memory (RAM) 22, while the control program is stored in read only memory (ROM) 21. Reprogramming is accomplished through the use of an external system programmer 28 having an RF transceiver wand 27, although a convention serial data port with lead connectors extending through the skin of the patient may also be used.

The invention also includes time domain reflectometer (TDR) I/O control 23, which includes the circuitry necessary to generate a TDR pulse on the electrodes and to detect the resulting reflected voltage. A TDR applies a narrow pulse of current with a fast rise time (typically by a tunnel diode) to the electrode and monitors the resulting reflected voltage on the electrode over a period of time. A stored reflected voltage waveform comprises a raw TDR reading. If the electrode has a known propagation velocity ($V_p$), the time delay to a particular reflection may be interpreted in distance from the pulse generator. This would include the pacemaker's internal wiring to the pacing electrode connectors, the electrical connection between the connectors and the pacing electrode, and the entire length of the pacing wire, terminating in the portion placed in heart tissue. The amplitude of the reflected voltage is a function of the electrode impedance (admittance/conductance) and the applied pulse, and therefore can be interpreted in dB, or in millirho, which is a function of impedance. Circuitry for time domain reflectometers is well-known and, in isolation, do not form the present invention. In general, a TDR comprises an I/O controller, a digital timebase, an analog timebase, and a pulse generator. As described further below and shown in FIG. 8, the TDR generates a short, fast rise time output pulse. After a predetermined amount of time has passed (the TDR base time), the pulse as reflected back by the wire/electrode is monitored. This comprises means for deferring the storing of the TDR signal until the amount time specified by the TDR base time signal has elapsed after the generation of a TDR incident pulse. At a specific time, as determined by the digital timebase, a portion or "slice" of the reflected wave is stored in an analog timebase. This value is then converted to a digital value by an analog to digital converter and stored in memory. The pulse generating-wave storing process is repeated, except that the time period between the pulse generation an when a portion of the reflected wave is stored is increased slightly, causing a different "slice" of the reflected wave to be stored. After a sufficient number of samples (e.g., 256) have been collected, a compilation of the stored waveform readings (a "TDR reading") provides a view of the entire reflected wave. A representative TDR pulse may comprise a 300 mV amplitude into a 50 ohm load, with a 25 microsecond pulse duration, and the reflected rise may be detected in less than 200 picoseconds.

In general, the present invention operates in the following manner. Logic and control 11 is designed to periodically send pacing signals via output line 24 to output section/voltage multiplier 13. Logic and control section 11 is programmed to cause output section/voltage multiplier to generate cardiac stimulating pulses of predetermined amplitude, duration and frequency according to parameters stored in RAM 22. A typical cardiac pacemaker generates stimulating pulses at frequencies of 0.5 to 3 per second, at amplitudes from 2.5 V to 8.5 V, and at durations of 0.15 to 2.3 milliseconds. Accordingly there is a substantial time gap of at least 300 milliseconds between pulses. As a complete TDR pulse and reflection reading time can be accomplished with a pulse repetition rate of 200 microseconds, it is possible to take an entire set of 256 readings in well under 60 milliseconds. Thus a complete TDR reading can be generated between the stimulating pulses periodically provided to the pacing electrode. However, it is also within the scope of the invention to space out the TDR pulses between multiple stimulating pulses.

Prior to implantation of the device in body, the device will be programmed with various default parameters. Conventional pacemakers are programmed, for example to specify the stimulating pulse repetition rate, pulse amplitude, positive and negative sensitivities and control mode. Prior to implantation, one or more pacing electrodes will be selected and connected to pacing leads 14, 15 and 16, 17 of the pacemaker. Each model of electrode has its own characteristics, including a textual model number, polarity, number of filaments, electrical length, physical length, $V_p$ and source resistance. Representative electrode parameters to assist in taking later TDR readings, are shown as electrode menu options 40 in FIG. 2. In addition, each electrode will ideally have a set of default sampling 41 and display 42 options. Preferably, the electrode parameters, sampling and display options may be specified by the electrode manufacturer and used to set default values in the pacemaker prior to implantation. Storing these parameters into the pacemaker is accomplished using conventional telemetry programming equipment with appropriate software to carry out the functions described herein.

To program the default electrode, sampling and display options into the pacemaker, external programmer 28 is first turned on, and the telemetry head of wand antenna 27 is positioned over the pacemaker. The telemetry head generates a magnetic field which activates reed switch 25 inside the pacemaker. This switch causes logic and control unit 11 to activate program receiver 19 and to receive instructions from programmer 28. In one embodiment of the invention, programmer 28 has a touch screen and various options are selected by touching the indicated portion of the screen. The physician will initially step through the prompts displayed on programmer 28 to transmit the desired pacemaker settings (e.g. stimulation rate, pulse amplitudes, sensitivities and mode) into the pacemaker. The physician may then select a TDR option on programmer 28, which will cause programmer 28 permit the TDR parameters to be specified and displayed, such as through the TDR options screen shown in FIG. 2.

The physician will initially wish to specify the default TDR values to be stored in the pacemaker. Ideally, programmer 28 will include a database of electrode manufacturers and models, with default electrode, sampling and display options for each electrode model. The database may be periodically updated by programmer 28 manufacturer via a floppy disk with information concerning new electrodes on the market. When the physician first enters the TDR menu, the top "Read Configuration for Pacemaker" option will be highlighted in reverse video. To select a default electrode configuration from the database, the physician presses down arrow 43 to cause the "Select Configuration from Electrode Database" option to be highlighted. The physician then depresses the Select button 50 on the screen. This causes an overlapping window to be displayed on the screen as shown in FIG. 4, displaying a list of electrode manufacturers and model numbers. The physician may repeatedly depress the down arrow until the electrode to be implanted is highlighted, then depress the Select option 50 on the touch screen. This will close the display window, and cause the Electrode, Sampling and Display options to be set to the default values recorded in the database for the particular electrode. While in this window (or any other window which may be opened) at any time prior to depressing the Select option 50, the physician may depress the Escape 47 portion on the screen, which will close the window and cause the display to revert to its previous status. A representative window and set of electrode default information values is shown in FIG. 1. Should the physician desire to change any of the default values, the physician may repeatedly depress the down arrow until the value to be changed is highlighted. The physician may then depress the left 48 and/or right 49 arrows, which will cause the highlighted values to be decremented or incremented, respectively.

After the physician has specified the desired electrode configuration values, the physician may store them in the pacemaker so that they do not have to be reprogrammed each time a TDR reading is taken. This is done by depressing the up or down arrows until the "Store Configuration to Pacemaker" option is selected. The Select button is then depressed, which causes all of the displayed electrode information to be transmitted to the pacemaker by RF transceiver 27 and stored in RAM 22. If the pacemaker provides means for connecting to a second electrode or wire, such as for multiple leads, or includes two leads for single bipolar electrode (i.e. a pulse/cathode and a ground/anode) then the pacemaker RAM 22 may be configured with sufficient memory to store a separate setting for each electrode or lead. (It should also be noted that a singe electrode can comprise a multi-filament wire.) In addition, pulse selector will include switch means for selecting whether the time domain reflectometer is operably connected to the means for connecting the first implantable electrode or the means for connecting to the second implantable electrode. The location for each storage will be designated by the "Electrode No." option in FIG. 2. If a pacemaker having capability for storing only one set of electrode readings receives an instruction and data to store electrode settings for an electrode other than no. 1, the number information may be ignored and the values replaced by the received values.

After this information has been specified, and prior to implantation, the physician may take an initial TDR reading. This is done by using the up and down arrows to highlight the "Obtain TDR Reading" option, the depressing the Select option 50 on the touch screen. This action causes programmer 28 to transmit a command to the pacemaker commanding the pacemaker to take a TDR reading according to the parameters stored in RAM 22.

Figure 8:
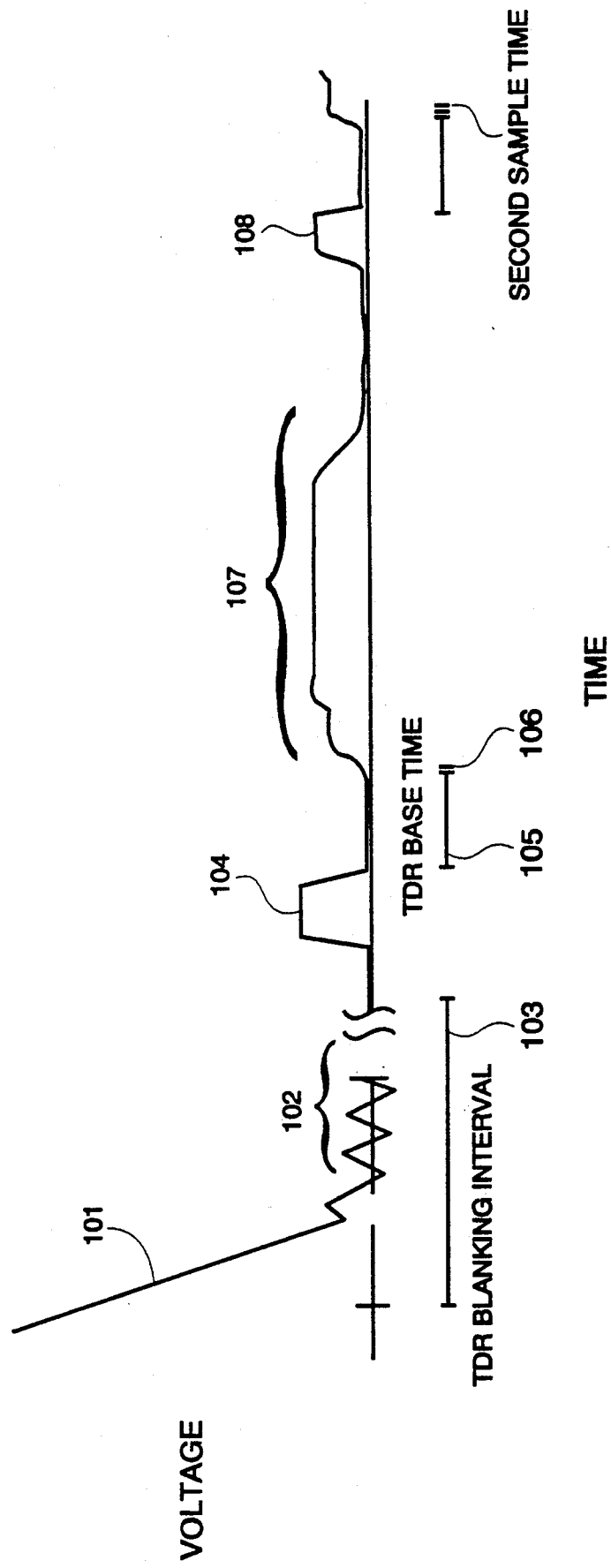
FIG. 8 is a representative time graph showing the trailing end of a stimulating pulse on the electrode, a TDR incident pulse, and reflective pulse.

When the pacemaker receives an instruction to take a TDR reading, the pacemaker waits until no stimulating pulse is present on the electrode. Referring to FIG. 8, normally, if stimulating pulses are being generated on a periodic basis, logic and control unit 11 will wait until the trailing edge of stimulating pulse 101 has been generated. Because stimulating pulse 101 may cause noise to be present on the electrode for a short time period after the pulse is generated, no action is taken during the time previously specified as TDR Blanking Interval 103. This system comprises means for deferring generation of the TDR incident pulse until the amount of time specified by the TDR blanking interval has elapsed after the transmission of a stimulating pulse on the electrode, or the detection of an identified physiological event. For stimulating pulse electrodes, this allows voltage on the electrode to completely drain until the TDR reading process begins. Also, some sensing electrodes, such as those used to monitor heart activity, may have a rhythmic voltage on them generated by an internal organ. Such electrodes are used, for example, to monitor cardiac activity, and logic and control unite 11 section of the pacemaker is capable of determining, at any point in time, the status of the rhythmic activity. For such electrodes, it is desirable to time each TDR reading to begin at the same time in the rhythmic cycle so that each TDR reading is taken at the same time of the rhythmic cycle, and therefore less subject to noise. For a cardiac sensing electrode, TDR blanking interval 103 may begin after completing of physiological event such as the atrial beat, as sensed by logic and control 11, and last for 300 milliseconds. After the 300 millisecond blanking interval, the TDR reading (or readings) may be made, as further described below, and the readings may be completed before the ventricular beat begins. This method, in combination of the minimal current needed to generate a TDR incident pulse, minimizes the likelihood of causing an irregular heartbeat. This system constitutes an anti-coincidence detector adapted to prevent a stimulating signal or physiological event from interfering with the incident pulse signal generated by the time domain reflectometer and its reflected wave.

After the TDR blanking interval has passed, logic and control system 11 sends an signal to pulse selector unit 26, which causes the electrode leads to be switched from an electrical connection with output section 13 to the TDR I/O and control section 23. (During normal pacemaker operation, TDR I/O and control 23 is insulated by pulse selector 26 from the stimulating pulses, to minimize the possibility that the relatively large currents and voltages of the stimulating pulses will harm the TDR circuitry. Also, as described below, pulse selector unit 26 may also operably connect TDR 23 with either X 134, Y 135 or Z 136 motion axis probes.) Logic and control 11 then sends a signal to TDR I/O and control 23, which comprises means for transmitting an electrical signal to the electrode receiving means, commanding the TDR to generate an incident pulse 104 (see FIG. 8) on the selected electrode lead.

In one embodiment of the invention, logic and control section 11 may include in the signal it sends to TDR I/O 23 a signal representing a impedance through which the TDR pulse should be sent. Ideally, the impedance equals the impedance of the electrode. Accordingly, TDR I/O 23 may include an internal array of source resistors of various impedances through which an incident pulse may be transmitted, and be connected to a multiplexor to select which resistor the pulse should be transmitted. This provides a preferred TDR reflection waveform.

After generation of incident pulse 104, TDR I/O waits the amount of time represented by TDR Base time 105. Normally, this amount of time will be selected to represent the amount of time it will take for a reflected pulse to be detected by TDR I/O 23, and may be on the order of 1-10,000 nanoseconds, depending on the electrical characteristics and length of the electrode. After TDR Base Time 105 passes, the TDR stores analog voltage detected 106 on the electrode in an analog timebase. Voltage 106 represents only a small portion of the entire reflected waveform 107. This analog voltage value is then converted to digital format by an analog-to-digital converter in TDR I/O 23, and then transmitted to logic and control section 11 for storage in output device, such as RAM 22. After a predetermined amount of time, such as 200 microsecond from the initiation of the first incident pulse, TDR I/O 23 generates second TDR pulse 108. The above process is repeated numerous (e.g. 256) times, except the time at which an analog voltage reading is stored in the analog timebase is incremented slightly with each cycle. As a result, RAM 22 has stored in it a raw TDR reading representing the reflected waveform.

After the TDR reading has been generated, logic and control section 11 sends a signal to pulse selector 26 causing the electrode connectors 14, 15 and/or 16, 17 to be electrically reconnected to the output section 13, and electrically disconnected from TDR I/O 23. The isolation of TDR I/O 23 from output section 13 by pulse selector 26 guards against any damage to the circuitry of TDR I/O 23 from stimulating pulses generated by output section 13. Thereafter, the generation of stimulating pulses may resume.

If the number of readings averaged parameter is greater than one, then the TDR reading process may be repeated, either immediately, if the time until the next stimulating pulse to be generated is sufficiently long, or else after the next stimulating pulse is generated. Taking multiple TDR readings and averaging them reduces any noise that may be inherent in a single reading. For averaged readings, instead of storing the each set of individual TDR waveform readings to the same RAM address, the digital values may be added to the previously stored values. After the total number of TDR readings specified by the "No. of Readings Averaged" parameter has been completed, the each sum may be divided by the number of readings comprising the sum to obtain a composite reading, namely the average. Alternatively, it is envisioned that merely the raw TDR readings may be transmitted to programmer 28 as described below, and programmer 28 perform the averaging of the readings.

It will be appreciated from the description of the foregoing embodiment that the time domain reflectometer, i.e. the system for generating incident pulses and storing the reflected wave form, comprises a logic and control system as is already found in conventional pacemekers, as well as TDR I/O circuitry. Moreover, a break in an electrode can also be detected merely by measuring the time interval between the beginning of the incident pulse and the beginning of the reflected waveform.

Figure 7:
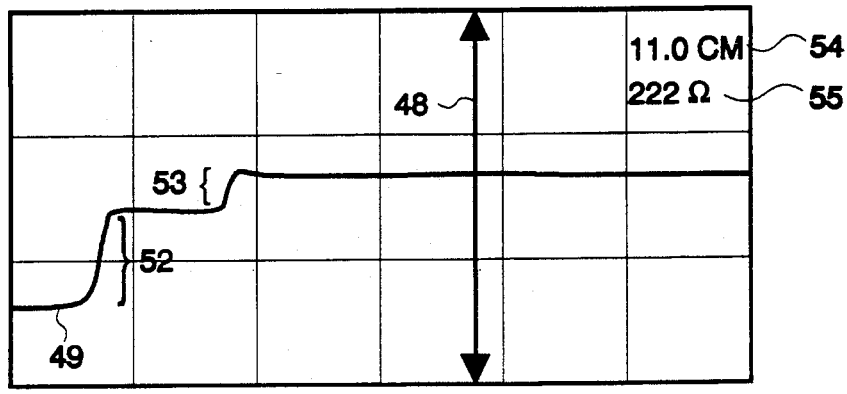
FIG. 7 is a representative graphically displayed TDR reading for an electrode have a short in it.

After the raw or composite TDR reading has been stored in RAM 22, logic and control section 11 transmits the stored raw or composite waveform through TDR reading output signal means, such as transceiver means comprised of telemetry transmitter 18 and antenna 20, to wand 27 of programmer 28. In addition, in the preferred embodiment, logic and control section 11, will also transmit to programmer 28, the stored sampling values used to take the TDR reading to programmer 28. This transmission assures that the correct parameter values may be displayed in association with the TDR reading. Programmer 28 then displays the received TDR reading in graphical form on a monitor (in graphical display window 411) or a printer, or both. Preferably, programmer 28 includes a Print button which when depressed, causes the displayed graph, and current configuration information to be printed. A representative TDR waveform for a working electrode is shown in FIG. 7. The horizontal axis represents the time, or sequential samples of the TDR reading, which can be directly converted into electrode distance if the $V_p$ of the electrode is known. As discussed above, this information may be supplied by the electrode manufacturer or manually programmed into the programmer. With a known $V_p$, the vertical gridlines, or divisions, represent a specific length from the TDR I/O output to the end of the electrode. The vertical axis of the waveform represents millirhos, which is directly convertible into impedance. Thus, a rise in the waveform represents increased resistance along the electrode, while a fall in the waveform represents a short circuit between the electrode and the pacemaker ground.

Accordingly, for the representative waveform shown in FIG. 7, waveform rise 52 represents an increase in resistance, which in this representative case, is attributable to the internal pacemaker wiring connection between the application specific integrated circuit on which pacemaker circuitry is connected and the wires connected to the pacing leads 14, 15, and 16, and 17. Second waveform rise 53 is attributable to the interconnection between electrode receptacle and the electrode plug. Thereafter, the waveform is flat, indicating a constant impedance throughout the length of the electrode, with no breaks or shorts.

Figure 5:
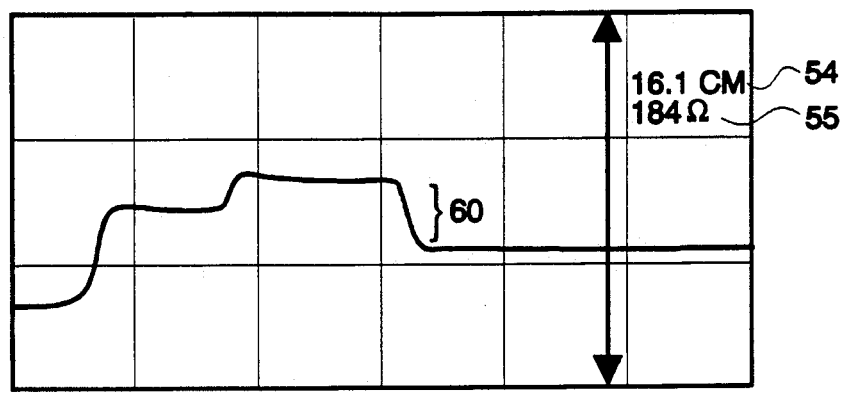
FIG. 5 is a representative graphically displayed baseline TDR reading for an electrode in good condition.

FIG. 5 shows a representative TDR reading in which the electrode has a partial short and is in need of replacement. Such a short may be caused, for example, by defective insulation between the leads/wires of a bipolar electrode, or by the exterior insulation of the electrode becoming worn by, for example, excessive rubbing against a bone, pacemaker case or other structure. The short is evident by waveform fall 60, indicating the impedance of the electrode at that point has fallen.

At anytime while a TDR Reading is displayed, the physician may depress the cursor left 45 or cursor right 46 arrows below the display to cause graphical cursor 48 to move left or right. At the point where cursor 48 intersects waveform 49, the distance of the electrode circuit and impedance of the waveform are shown in displays 54 and 55. Thus, cursor 48 and displays 54 and 55 comprise means for superimposing a distance scale measurement corresponding to the length of the implanted electrode on the graphical display.

Figure 2:
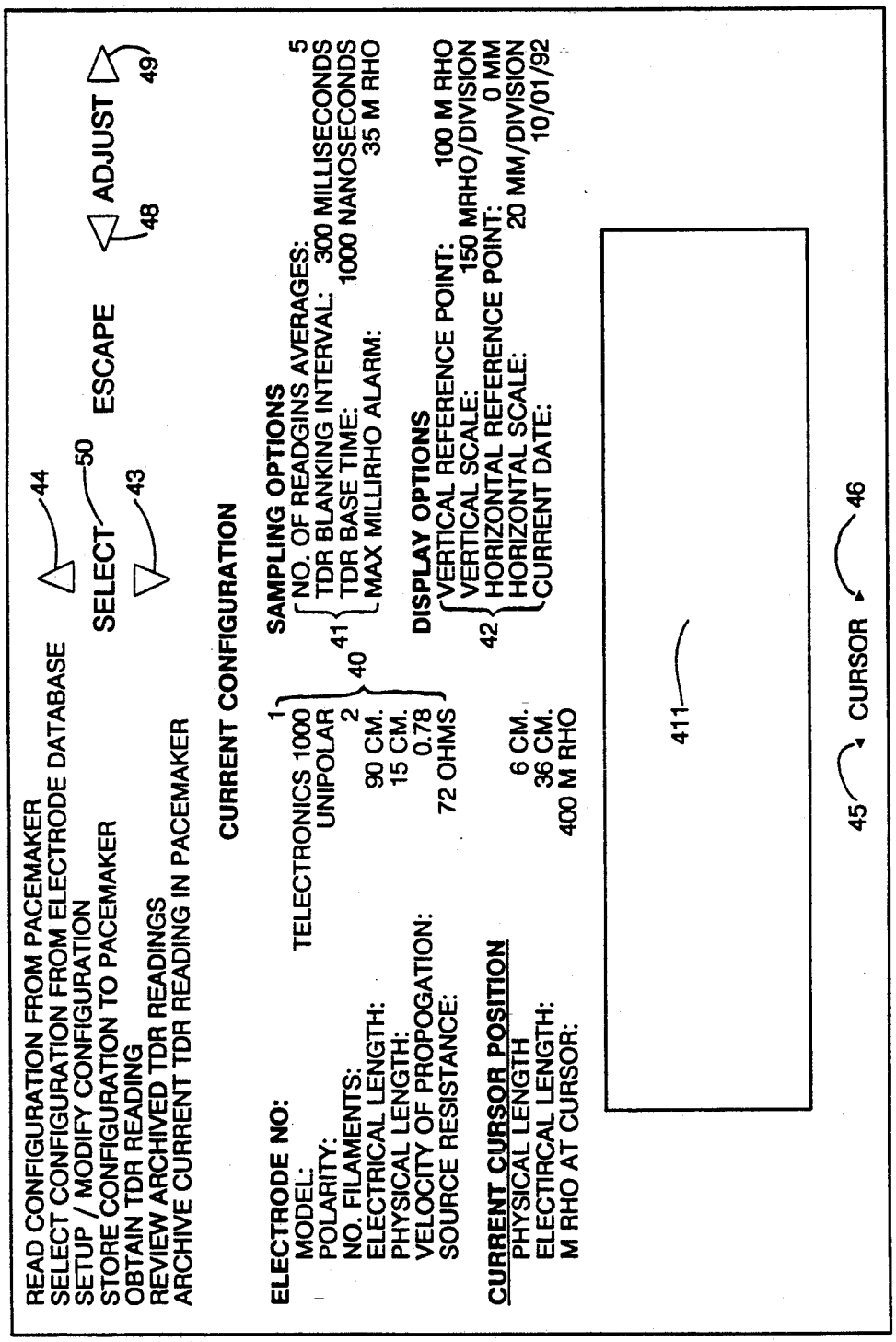
FIG. 2 a representative computer touch screen user interface for configuring and testing an implantable electrode according to the invention.

After the physician has obtained and displayed the composite TDR reading, the reading may be transmitted back to the pacemaker and stored in RAM 22, which comprises means for storing multiple TDR output signals. As shown in FIG. 2, this may be done by depressing the down arrow until the "Archive Current TDR Reading in Pacemaker" menu option is highlighted. The Select button is then depressed. This causes programmer 28 display a dialogue box on the screen in which the physician may type a short descriptive summary of the reading using a keyboard connected to programmer 28, such as "Pre-implant readings w/Technitronics 1000", and in which the physician may enter his or her name. After this option information has been entered, the Select button is again depressed, causing programmer 28 to transmit the TDR waveform, along with the Sampling Options, Display Options and textual information (including the date, which comprises a means for associating each stored output signal with a time reference indicating when the output signal is generated) through wand antenna 27 to antenna 20 of the pacemaker, accompanied by a command instructing the pacemaker logic and control 11 to store the information in RAM 22. This stored reading may be used as a baseline TDR reading against which future TDR readings may be compared to assist in evaluating electrode integrity. In one embodiment, RAM 22 has sufficient capacity to store up to 512 TDR readings and associated information. Logic and control 11 stores in RAM 22 an incremental counter indicating the total number of readings that have been stored in RAM 22 and the address of the next subsequent reading to be stored.

Assuming the initial TDR reading is acceptable, the physician may proceed with implantation of the pacemaker and electrode. Following implantation, but prior to closing the surgical incision in the patient, the physician may take a second TDR reading to ensure that no damage to the pacemaker or electrode occurred during implantation. Assuming the TDR reading is acceptable, the physician may close the incision.

Following implantation, the patient can be expected to have numerous follow-up visits with the physician, during which the integrity of the implanted electrode may be evaluated. This may be done using the same programmer 28 described above. After the programmer is turned on, wand 27 is positioned over the patient's pacemaker, and the TDR option is selected, the screen shown in FIG. 2 may appear. The physician choose to first retrieve a copy of the archived TDR reading from when the electrode was first implanted. This may be done by using up 44 and down 43 arrows to highlight the "Review Archived TDR Readings" option, and depressing Select. This will cause programmer 28 to send a signal to the pacemaker instructing logic and control section 11 to transmit the archive number, date, comment and physician portions of each archived TDR reading to the programmer. An archived TDR display window, as shown in FIG. 3 is then displayed. Using up 44 and down 43 arrows, the physician may highlight an archived TDR reading, which will normally be the baseline reading or first reading archived after implantation. Depressing the Select portion of the screen causes programmer 28 close the window and to command the pacemaker to transmit the selected archived TDR reading (including the electrode, sampling and display options) to the programmer, where they are displayed. The physician may then depress the up arrow to highlight the "Obtain TDR Reading" menu option, then press Select 50. This will cause a TDR reading to be generated as described above, and superimposed over the archived TDR reading.

By highlighting and adjusting the "Max MIllirho Alarm" option, the physician may specify a millirho value (predetermined threshold) by which, if a TDR reading deviates in a relevant portion, an indicating output warning signal, such as a flashing light, buzzer, or "DEFECTIVE" screen display is generated. High and low limits from the electrode portion of the display waveform may be represented as horizontal lines on the graphical display. Specifically, minimum warning line 64 and maximum warning line 65 as shown in FIG. 67 define the boundaries in which the entire electrode portion of the waveform is expected to fall. If a waveform deviates from these limits, DEFECTIVE legend 66 may be displayed on the screen, preferably in a highly contrasting color and accompanied by an audible alarm.

Figure 6:
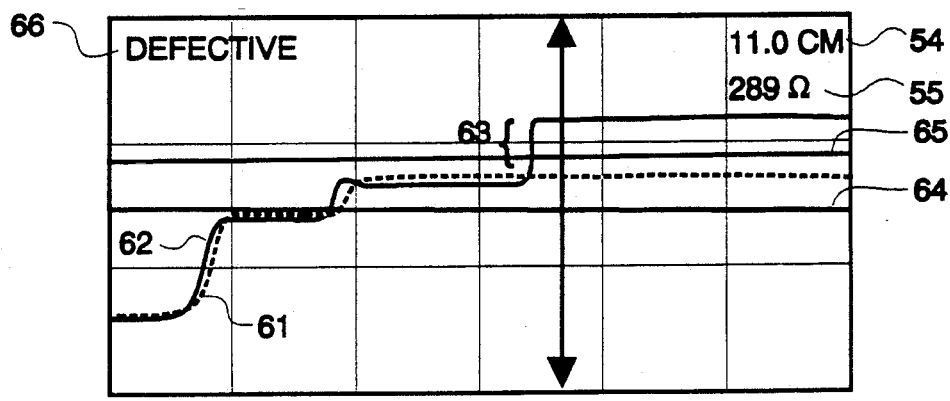
FIG. 6 is a representative graphically displayed baseline TDR reading having superimposed over it a more recent TDR reading for the same electrode showing that a break has occurred in the electrode and that the electrode is now defective.

FIG. 6 shows a representative superimposed TDR reading, in which archived reading 61 shows an electrode in good condition, while current reading 62 shows that the electrode has broken. Specifically, reading 62 includes waveform rise 63, indicating that the impedance of the electrode has risen. This may be caused by, for example, a filament becoming cracked or completely severed. Because current reading 62 exceeds maximum alarm level 65, DEFECTIVE legend 66 is displayed on the screen, alerting the physician that the electrode may be defective.

The current Configuration parameters 40, 41 and 42 shown in FIG. 2, as mentioned above, may be adjusted. With regard to Display Options 42, these parameters effect how a particular TDR reading is displayed on the screen. In particular, different electrodes from different manufactures and for different purposes will generate TDR readings have different impedance baselines and lengths. In order to scale a TDR reading on the graphical display, the Vertical and Horizontal reference points and scales may be adjusted. These values will also be stored along with an archived TDR reading so that when the reading is retrieved, it will be initially displayed using the same viewing parameters as when it was stored.

It will be appreciated to those of skill in the art that may changes could be made in the foregoing representative embodiment without departing from the spirit and scope of the invention. For example, the present invention may be used with virtually any type of implantable electrode, such as ventricular, rate sensing, morphology, high voltage, mapping, sensor, temporary, ablation and angio/artheretomy electrodes or patient cables. The invention may also be used in connection with wires used in connection with devices such as implanted insulin pumps, and such wires are within the scope of the term "electrode" as used herein and in the claims. In addition, in instances where a tube or stint is implanted in a patient, a tube configured with an embedded electrical conductor running the length of the tube and connectable to a TDR, and which will break if the tube breaks, is also included within the definition of an electrode as used herein.

It will also be appreciated that although the in the embodiment described above a TDR reading is output through RAM and an RF antenna, other transceiver or output means are within the spirit and scope of the invention. For example, virtually any other electromagnetic wave communication means may be used, at any desired frequency, including optical frequencies, or wire leads may be used to transmit a TDR reading. Alternatively, the system is useful for non-telemetering (non-RF) systems, such as pacing system analyzers used during implants of cardiac pulse generator or AICD's. Moreover, the TDR reading described above is obtained by generating multiple incident pulses and storing a small portion of each reflected pulse. It is contemplated that with the development of faster electronic and CPU circuitry, that a TDR reading may possibly be generated by storing the reflected wave from a single incident pulse, and such systems included within the definition of a TDR. It will also be appreciated that in the embodiment described above, a user-selected number of multiple raw TDR readings may be averaged to produce a composite reading to eliminate noise associated with individual readings. The averaging function could easily be transferred from the internal implantable device to external programmer 28. Moreover, other manipulations of raw TDR readings, such as by averaging multiple readings, would not necessarily alter their definition as being a TDR reading. Other functions contemplated to be performed by the pacemaker could also be performed by external programmer 28. For example, the storage of TDR readings could be performed on external programmer 28, and optionally, may be indexed by a unique key, such as patient social security number or pacemaker serial number, to distinguish between stored readings from different patients. Also, graphical display of programmer 28 may include means for displaying the amplitude differential between the incident pulse and a selected portion of a TDR reading.

An important feature of the present invention is that the TDR may be used not only to test the integrity of an electrode, but also to provide a responsive heart stimulating system. This is done by performing additional analysis of the TDR readings from an implanted electrode which detects an increase in heart stroke volume. Alternatively, or in addition, the TDR may also be operatively connected to TDR probes in an enclosed chamber containing a flowable substance, which operates as a motion detector. The conclusions reached from analyzing the implanted electrode and/or motion sensor TDR readings may be used to automatically adjust the waveform of a heart stimulating device, by, for example, increasing or decreasing the pacing rate of a pacemaker.

Referring to FIG. 9a there is shown a heart 120 during its minimum stroke volume in which a pacing electrode 121 is implanted. As heart 120 beats, it continually expands and contracts. FIG. 9b shows heart 120 at its maximum stroke volume, as evidenced by the increased size of lower heart portion 122. It is known that when a person undertakes physical activity, their maximum heart stroke volume normally increases. This is generally true even for persons suffering from chronotropic incompetence, whose pulse rate does not sufficiently increase with increased physical activity. Thus, detection of a change in maximum heart stroke volume can be used in increase or decrease a pacemakers pace rate, or to otherwise alter the waveform generated by a heart stimulating device.

In one embodiment of the present invention, a change in heart stroke volume can be detected by generating a TDR reading from the implanted electrode timed from a physiological event or stimulation pulse, or when the heart is at or near its maximum stroke volume. Detection of when a heart is at or near its maximum stroke volume by monitoring implanted electrode is known in the art, and is used, for example, in existing bipolar heart stroke volume detectors.

A change in heart stroke volume using a TDR reading is possible in part because, as the heart continually expands and contracts, the end 123 of a pacemaker electrode is stretched and contracted. When the electrode end 123 is stretched, this results in a slightly lower conductance (higher resistance) in the stretched portion of the electrode. As stroke volume increases, the stretching of electrode tip 123 will correspondingly increases, as will its resistance. When the electrode tip resistance during the stroke volume has increased by a certain level, an adjustment in the heart stimulating waveform, such as an increased pacing rate, may be performed. Also, when the electrode tip resistance during the stroke volume has decrease by a certain level, the waveform may also be altered, such as by decreasing the pacing rate.

As shown in FIG. 10a, a TDR reading from an implanted electrode taken during a heart's minimum stroke volume, when electrode tip 123 is not stretched, shows a fairly even resistance at TDR reading portion 124. When TDR reading is taken during the maximum stroke volume as shown in FIG. 10b, there is a slight increase in resistance at TDR reading portion 125, as evidenced by the higher waveform portion 126. As a patient undertakes increased physical activity, the maximum heart stroke volume will increase, stretching electrode end 123 more and more. This will result in increased resistance of electrode end 123 as shown by TDR reading portion 127. As maximum stroke volume continues to increase, TDR reading portion 128 will continue to rise. Once the TDR readings increase a sufficient amount, logic and control unit 11 may be used to cause the heart stimulating waveform to be altered, such as by increasing the pacing rate. Also, when a decrease is detected, the pacing rate may be reduced, or the waveform otherwise altered. Detection of a change in electrode tip resistance obviously requires that TDR readings be stored so that they may be compared to current TDR readings. This may be accomplished by logic and control unit 11 storing digital TDR readings in RAM 22. In one embodiment of the invention, a TDR reading may be taken during the maximum stroke volume approximately every ten seconds, and thirty readings may be stored in RAM. This may provide logic and control until 11 with sufficient historical data to determine when a change in maximum heart stroke volume has occurred.

A decision on when to alter the heart stimulating waveform may be made on any number of factors, and the specific method used does not constitute the invention per se. Algorithms for adjusting a heart stimulating waveform based on a change in heart stroke volume are known in the art. For example, after a pacemaker has been implanted and the patient is sufficiently healthy to undertake a stress test, a physician may monitor the TDR readings during the maximum stroke volume have telemetering the readings to an external programmer as described above. Of course, the programmer would include an option to take TDR readings at the approximate maximum stroke volume. By comparing TDR readings with the level of work performed by the patient, the physician may easily identify thresholds of electrode ends appropriate to cause an increase or decrease in the pacing rate, and may program such parameters into the pacemaker using an external programmer. Such a programmer may be used to specify a predetermined set of pacing rates, such as 60, 75, 90 and 105 beats per minute. Alternatively, a pacemaker may be programmed to automatically increase or decrease the pacing rate based on the extent to which the maximum heart stroke volume is between its levels when the patient is at rest and when the patient is engaged in strenuous physical activity. For example, the pacing rate could continuously vary between a baseline and maximum level, based on a baseline and maximum maximum heart stroke volume, to thereby provide a pacemaker that is responsive to a patient's heart stroke volume.

It will also be appreciated that the specific portion of the TDR waveform that is responsive to changes in maximum stroke volume will vary with parameters such as the brand and model of electrode used and size of the patient's heart, and the exact position in the heart where the electrode is implanted. Therefore, the physician, after viewing the results of TDR readings taken during a stress level test, may choose to program which portion of the TDR reading should be subject to processing to determine a change in stroke volume. For example, assuming a TDR processor is used that breaks up each reading into 256 individual reading, examination of readings may indicate that readings 150-200 are most representative of the portion of the electrode subject to stretching during the stroke volume period. In another patient or when a different electrode is used, readings 180-210 might be most appropriate. Such parameters may be programmable into the pacemaker using a programmer, software and telemetering techniques well-known in the art.

It will also be appreciated that the present invention may be used with either endocardial or epicardial electrodes. When an epicardial electrode is used, the physician should ensure that the electrode is implanted against the exterior wall of the heart having the greatest movement during the heartbeat.

In order to minimize the likelihood of incorrectly interpreting TDR readings, the above-waveform altering system may also incorporate motion sensor readings. Combining motion sensor readings with readings from other physiological readings to determine when an adjustment in a pacing rate is warranted is also known in the art. However, the present invention allows motion sensor readings to be taken by a TDR, which may already be a component of a pacemaker, thus making additional specialized circuitry unnecessary. Moreover, as TDR readings require much less energy than conventional resistance-based or opto-electric based readings, battery life is extended.

Referring to FIG. 11, there is shown a vertical cross sectional view of a TDR motion sensor in accordance with the present invention. Specifically, enclosed chamber 130, which is preferably formed from a substantially non-conductive material, includes two slotted lugs 131 and 132 for physical connection to a pacemaker header can by screws 133. Alternatively, enclosed chamber may be implanted separately from pacemaker and connected thereto by electrodes. Enclosed chamber 130 includes conductive contact points, namely, three metal TDR probes, namely X-axis probe 134, Y-axis probe 135, and Z-axis probe 136, each of which is sealingly engaged in the wall of enclosed chamber 130 and connected to a separate wire. Within enclosed chamber 130 is a flowable substance, such a saline solution 137. In one embodiment, solution 137 occupies approximately 35% of the volume of enclosed chamber 130. It will be appreciated that as enclosed chamber 130 moves, solution 137 will move within chamber 130 and contact different portions of probes 134, 135 and 136. As different portions of these probes are contacted, their conductive properties as detected by a TDR reading will change. FIGS. 13, 14, and 15 are TDR readings for probes indicating, respectively, no, moderate, and heavy movement as sensed by a single probe. The techniques used to analyze the relevant TDR reading of each probe signal may be the same used to analyze accelerometer or piezoelectric motion detector signals. Specifically, the portions of the TDR readings representing the probe portion within enclosed chamber 130 over 0.5-2 minutes may be processed using well-known analysis of variance techniques, such as those described in *Bendat and Piersol*, Random Data: Analysis and Measurement Procedures, Wiley-Interscience (1971) or *Spiegel*, Schaum's Outline of Theory and Problems of Probability and Statistics, McGraw-Hill (1975), which are incorporated herein by reference. When such analysis indicates that a sufficient level of movement has occurred, logic and control unit 11 can cause a change in the pacing rate. In order to obtain a more accurate indication of the total movement and to filter out noise in readings, all three probes may be processed to generate a composite variance reading. Of course, the specific thresholds appropriate to justify a change in pacing rate will vary with materials used and sizes of the probes, the conductivity of enclosed chamber 130 flowable material 137, and the pacing levels appropriate for the particular patient as determined by a qualified physician.

It will further be appreciated by those of skill in the art that the heart stroke volume detection system may be combined with the motion detection system to provide a responsive system based upon two different parameters. Moreover, the heart stimulating waveform may altered not just by varying the pacing rate, but by changing other waveform characteristics such as amplitude, pulse shape (i.e. square, triangular or sinusoidal) or pulse width. Moreover, with any of the aforementioned TDR "readings," such readings may include a composite reading generated by averaging the values of multiple individual TDR readings to reduce noise. In addition, to obtain a normalization of multiple TDR readings to generate a composite reading, several TDR readings may be taken using incident TDR pulses have different leading edge rise times (preemphasis), and the resulting waveform readings averaged.

What is claimed is:

1. A responsive heart stimulating device, comprising:
   means for generating a heart stimulating waveform and transmitting the waveform to an electrode receiving means,
   a time domain reflectometer (TDR) for generating TDR signals, the TDR being operatively coupled to the means for generating a heart stimulating waveform;
   processor means for processing the TDR signals, the processor means operatively connected to the TDR and to the generating means;
   means for altering the waveform based on the processing of the TDR signals.

2. The device of claim 1 wherein the heart stimulating device comprises a pacemaker.

3. The device of claim 2 wherein the heart stimulating waveform comprises heart pacing pulses.

4. The device of claim 3 wherein the means for altering comprises means for altering the rate of the heart pacing pulses.

5. The device of claim 4 wherein the means for altering the rate of the heart pacing pulses comprises means for selecting a pacing rate from a set of predefined pacing rates.

6. The device of claim 3 further comprising a pacing electrode connected to the electrode receiving means, and wherein the means for altering is responsive to the conductance of the electrode.

7. The device of claim 6 further comprising:
   means for determining when a heart is at a predetermined point in a heart cycle,
   and wherein the generating means includes means for generating a TDR signal when the heart is at the predetermined point in the heart cycle.

8. The device of claim 7, wherein the predetermined point in the heart cycle comprises the maximum stroke volume point.

9. The device of claim 3 further comprising:
   an enclosed chamber comprising an interior surface,
   a flowable substance within the enclosed chamber,
   a plurality of conductive contact points on the interior surface, the conductive contact points on the interior surface, the conductive contact points being contactable by the flowable substance and operably connected to the TDR such that a TDR signal from a contact point changes when the enclosed chamber moves.

10. The device of claim 1 wherein the TDR is operatively connected to the electrode receiving means.

11. The device of claim 1 wherein the device comprises a defibrillator.

12. The device of claim 1 wherein the device further comprises:
   an electrode connected to the electrode receiving means such that the TDR signals and generated pacing waveforms may be transmitted to the electrode.

13. The device of claim 1 wherein the generated waveform comprises pulses and wherein the altering means comprises means for altering the shape of each pulse of the waveform.

14. The device of claim 13 further comprising means for comparing stored TDR signals.

15. The device of claim 13 further comprises means for telemetering stored TDR signals to an external receiver.

16. The device of claim 1 further comprising a means for storing the TDR signals.

17. A method for altering a waveform of a heart stimulating device, the stimulating device including time domain reflectometer (TDR) means for generating TDR signals, processor means operatively connected to the time domain reflectometer for processing the TDR signals, means for generating a heart stimulating waveform, means for altering the waveform, the method comprising:
   generating a TDR signal;
   processing the TDR signal;
   altering the heart stimulating waveform based upon the processing of the TDR signal.

18. The method of claim 17 wherein the processing step includes the step of comparing the generated TDR signal to a reference TDR signal.

19. The method of claim 17 wherein the TDR is operatively connected to an electrode receiving means.

20. The method of claim 19 wherein the altering step comprises altering the rate of pulses of the heart stimulating waveform.

21. The method of claim 20 wherein the stimulating device further comprises a pacing electrode operatively connected to the TDR, and wherein the altering step is responsive to the conductance of the electrode.

22. The method of claim 20 further the steps of:
   determining when a heart is at a predetermined point in a heart cycle, and wherein
   the generating step comprises generating a TDR signal when the heart is at its approximate maximum stroke volume.

23. The method of claim 22 wherein the predetermined point in the heart cycle comprises the maximum stroke volume.

24. The method of claim 20 further comprising the step of: providing:
   an enclosed chamber comprising an interior surface,
   a flowable substance within the enclosed chamber;
   a plurality of conductive contact points on the interior surface, the conductive contact points being contactable by the flowable substance and are operably connected to the TDR, and
   wherein the generated TDR signal is transmitted to at least one of the conductive contact points such that a TDR signal from the contact point changes when the enclosed chamber moves.

25. The method of claim 17 wherein the heart stimulating device comprises a pacemaker.

26. The method of claim 21 wherein the altering step comprises selecting a pacing rate from a set of predefined pacing rates.

27. The method of claim 17 wherein the device comprises a defibrillator.

28. The method of claim 27 further comprising the step of comparing stored TDR signals.

29. The method of claim 27 further comprises means for telemetering stored TDR signals to an external receiver.

30. The method of claim 17 wherein the generated waveform comprises pulses and wherein the altering step includes altering the shape of each pulse of the waveform.

31. The method of claim 17 further comprising the step of storing the generated TDR signals.

* * * * *